(12) United States Patent
Hawkins et al.

(10) Patent No.: US 9,402,737 B2
(45) Date of Patent: Aug. 2, 2016

(54) HIGHLY LORDOSED FUSION CAGE

(71) Applicant: DePuy Synthes Products, Inc., Raynham, MA (US)

(72) Inventors: John Riley Hawkins, Cumberland, RI (US); Anwar M Upal, Fall River, MA (US); Michael J O'Neil, West Barnstable, MA (US); Michael Andrew Slivka, Taunton, MA (US); Michael Fisher, Lawrenceville, GA (US)

(73) Assignee: DePuy Synthes Products, Inc., Raynham, MA (US)

(*) Notice: Subject to any disclaimer, the term of this patent is extended or adjusted under 35 U.S.C. 154(b) by 0 days.

(21) Appl. No.: 14/514,700

(22) Filed: Oct. 15, 2014

(65) Prior Publication Data

US 2015/0045894 A1 Feb. 12, 2015

Related U.S. Application Data

(62) Division of application No. 11/768,636, filed on Jun. 26, 2007, now Pat. No. 8,900,307.

(51) Int. Cl.
*A61F 2/44* (2006.01)
*A61F 2/46* (2006.01)
*A61F 2/30* (2006.01)

(52) U.S. Cl.
CPC .............. *A61F 2/4455* (2013.01); *A61F 2/442* (2013.01); *A61F 2/447* (2013.01); *A61F 2/4611* (2013.01); *A61F 2/30744* (2013.01); *A61F 2/30965* (2013.01); *A61F 2002/3008* (2013.01); *A61F 2002/30062* (2013.01); *A61F 2002/30331* (2013.01); *A61F 2002/30387* (2013.01); *A61F 2002/30579* (2013.01); *A61F 2002/30604* (2013.01); *A61F 2002/30685* (2013.01);
(Continued)

(58) Field of Classification Search
CPC ....... A61F 2/44; A61F 2/4455; A61F 2/4465; A61F 2/447
USPC ............................................ 623/17.11–17.16
See application file for complete search history.

(56) References Cited

U.S. PATENT DOCUMENTS

| 4,349,921 A | 9/1982 | Kuntz |
| 4,863,476 A | 9/1989 | Shepperd |

(Continued)

FOREIGN PATENT DOCUMENTS

| CN | 101909548 A | 12/2010 |
| DE | 4012622 | 7/1997 |

(Continued)

OTHER PUBLICATIONS

Gore, Technique of Cervical Interbody Fusion, Clinical Orthopaedics and Related Research, Sep. 1984, pp. 191-195, No. 188.

(Continued)

*Primary Examiner* — Matthew Lawson
(74) *Attorney, Agent, or Firm* — Baker & Hostetler LLP

(57) ABSTRACT

A fusion cage has a first component that defines an outside surface that is configured to engage a vertebral endplate, and an interior surface. The fusion cage has a second component that defines first and second opposed surfaces. One of the first and second opposed surfaces can mate with the interior surface of the first component. The fusion cage can include vertical and lateral throughholes adapted to enhance fusion.

30 Claims, 11 Drawing Sheets

(52) U.S. Cl.
CPC .................. *A61F2002/30841* (2013.01); *A61F 2002/30904* (2013.01); *A61F 2002/30975* (2013.01); *A61F 2002/448* (2013.01); *A61F 2002/4627* (2013.01); *A61F 2002/4629* (2013.01); *A61F 2210/0004* (2013.01); *A61F 2220/0025* (2013.01); *A61F 2250/0098* (2013.01); *A61F 2310/00017* (2013.01); *A61F 2310/00023* (2013.01); *A61F 2310/00029* (2013.01); *A61F 2310/00203* (2013.01); *A61F 2310/00239* (2013.01)

(56) References Cited

U.S. PATENT DOCUMENTS

| | | | |
|---|---|---|---|
| 5,059,193 | A | 10/1991 | Kuslich |
| 5,290,312 | A | 3/1994 | Kojimoto et al. |
| 5,344,252 | A | 9/1994 | Kakimoto |
| 5,370,697 | A | 12/1994 | Baumgartner |
| 5,390,683 | A | 2/1995 | Pisharodi |
| 5,443,514 | A | 8/1995 | Steffee |
| 5,522,899 | A | 6/1996 | Michelson |
| 5,534,029 | A | 7/1996 | Shima |
| 5,554,191 | A | 9/1996 | Lahille et al. |
| 5,609,635 | A | 3/1997 | Michelson |
| 5,653,763 | A | 8/1997 | Errico |
| 5,658,335 | A | 8/1997 | Allen |
| 5,665,122 | A | 9/1997 | Kambin |
| 5,697,977 | A | 12/1997 | Pisharodi |
| 5,716,415 | A | 2/1998 | Steffee |
| 5,772,661 | A | 6/1998 | Michelson |
| 5,782,832 | A | 7/1998 | Larsen et al. |
| 5,860,973 | A | 1/1999 | Michelson |
| 5,865,848 | A | 2/1999 | Baker |
| 5,888,224 | A | 3/1999 | Beckers et al. |
| 5,893,889 | A | 4/1999 | Harrington |
| 5,893,890 | A | 4/1999 | Pisharodi |
| 5,980,522 | A * | 11/1999 | Koros .................. A61F 2/4455 606/60 |
| 6,039,761 | A | 3/2000 | Li |
| 6,045,579 | A | 4/2000 | Hochshuler |
| 6,102,950 | A | 8/2000 | Vaccaro |
| 6,106,557 | A | 8/2000 | Robioneck et al. |
| 6,117,174 | A | 9/2000 | Nolan |
| 6,127,597 | A | 10/2000 | Beyar et al. |
| 6,129,763 | A | 10/2000 | Chauvin et al. |
| 6,146,387 | A | 11/2000 | Trott et al. |
| 6,176,882 | B1 | 1/2001 | Biedermann et al. |
| 6,179,794 | B1 | 1/2001 | Burras |
| 6,179,873 | B1 | 1/2001 | Zientek |
| 6,183,517 | B1 | 2/2001 | Suddaby |
| 6,193,757 | B1 | 2/2001 | Foley et al. |
| 6,296,647 | B1 | 10/2001 | Robioneck et al. |
| 6,302,914 | B1 | 10/2001 | Michelson |
| 6,332,895 | B1 * | 12/2001 | Suddaby .................. 623/17.11 |
| 6,368,351 | B1 | 4/2002 | Glenn |
| 6,375,682 | B1 | 4/2002 | Fleischmann et al. |
| 6,387,130 | B1 | 5/2002 | Stone |
| 6,409,766 | B1 | 6/2002 | Brett |
| 6,419,705 | B1 | 7/2002 | Erickson |
| 6,419,706 | B1 | 7/2002 | Graf |
| 6,436,140 | B1 | 8/2002 | Liu et al. |
| 6,454,806 | B1 | 9/2002 | Cohen et al. |
| 6,454,807 | B1 | 9/2002 | Jackson |
| 6,488,710 | B2 | 12/2002 | Besselink |
| 6,527,804 | B1 | 3/2003 | Gauchet et al. |
| 6,558,424 | B2 | 5/2003 | Thalgott |
| 6,562,074 | B2 | 5/2003 | Gerbec et al. |
| 6,582,468 | B1 | 6/2003 | Gauchet |
| 6,610,094 | B2 | 8/2003 | Husson |
| 6,641,614 | B1 | 11/2003 | Wagner et al. |
| 6,648,917 | B2 | 11/2003 | Gerbec et al. |
| 6,676,665 | B2 | 1/2004 | Foley et al. |
| 6,706,070 | B1 | 3/2004 | Wagner et al. |
| 6,719,796 | B2 | 4/2004 | Cohen et al. |
| 6,723,126 | B1 | 4/2004 | Berry |
| 6,733,532 | B1 | 5/2004 | Gauchet et al. |
| 6,743,255 | B2 | 6/2004 | Ferree |
| 6,805,714 | B2 | 10/2004 | Sutcliffe |
| 6,855,167 | B2 | 2/2005 | Shimp |
| 6,863,673 | B2 | 3/2005 | Gerbec et al. |
| 6,893,464 | B2 | 5/2005 | Kiester |
| 6,953,477 | B2 | 10/2005 | Berry |
| 6,955,691 | B2 | 10/2005 | Chae et al. |
| 6,969,404 | B2 | 11/2005 | Ferree |
| 6,969,405 | B2 | 11/2005 | Suddaby |
| 7,018,412 | B2 | 3/2006 | Ferreira et al. |
| 7,018,416 | B2 | 3/2006 | Hanson et al. |
| 7,037,339 | B2 | 5/2006 | Houfburg et al. |
| 7,083,650 | B2 | 8/2006 | Moskowitz et al. |
| 7,094,257 | B2 | 8/2006 | Mujwid et al. |
| 7,211,112 | B2 | 5/2007 | Baynham et |
| 7,217,293 | B2 | 5/2007 | Branch |
| 7,220,280 | B2 | 5/2007 | Kast et al. |
| 7,223,292 | B2 | 5/2007 | Messerli et al. |
| 7,226,483 | B2 | 6/2007 | Gerber et al. |
| 7,235,101 | B2 | 6/2007 | Berry et al. |
| 7,326,248 | B2 | 2/2008 | Michelson |
| 7,503,933 | B2 | 3/2009 | Michelson |
| 7,507,241 | B2 | 3/2009 | Levy et al. |
| 7,517,363 | B2 | 4/2009 | Rogers et al. |
| 7,569,074 | B2 | 8/2009 | Eisermann et al. |
| 7,618,458 | B2 | 11/2009 | Biedermann et al. |
| 7,621,950 | B1 | 11/2009 | Globerman et al. |
| 7,621,960 | B2 | 11/2009 | Boyd et al. |
| 7,691,147 | B2 | 4/2010 | Gutlin et al. |
| 7,703,727 | B2 | 4/2010 | Selness |
| 7,722,612 | B2 | 5/2010 | Sala et al. |
| 7,722,674 | B1 | 5/2010 | Grotz |
| 7,749,270 | B2 | 7/2010 | Peterman |
| 7,771,473 | B2 | 8/2010 | Thramann |
| 7,785,368 | B2 | 8/2010 | Schaller |
| 7,789,914 | B2 | 9/2010 | Michelson |
| 7,819,921 | B2 | 10/2010 | Grotz |
| 7,824,445 | B2 | 11/2010 | Biro et al. |
| 7,837,734 | B2 | 11/2010 | Zucherman et al. |
| 7,846,206 | B2 | 12/2010 | Oglaza et al. |
| 7,850,733 | B2 | 12/2010 | Baynham et al. |
| 7,854,766 | B2 | 12/2010 | Moskowitz et al. |
| 7,874,980 | B2 | 1/2011 | Sonnenschein et al. |
| 7,879,098 | B1 | 2/2011 | Simmons, Jr. |
| 7,887,589 | B2 | 2/2011 | Glenn et al. |
| 7,909,870 | B2 | 3/2011 | Kraus |
| 7,922,729 | B2 | 4/2011 | Michelson |
| 7,951,199 | B2 | 5/2011 | Miller |
| 7,985,231 | B2 | 7/2011 | Sankaran |
| 7,993,403 | B2 | 8/2011 | Foley et al. |
| 8,021,424 | B2 | 9/2011 | Beger et al. |
| 8,021,426 | B2 | 9/2011 | Segal et al. |
| 8,025,697 | B2 | 9/2011 | McClellan et al. |
| 8,034,109 | B2 | 10/2011 | Zwirkoski |
| 8,043,381 | B2 | 10/2011 | Hestad et al. |
| 8,062,375 | B2 | 11/2011 | Glerum et al. |
| 8,075,621 | B2 | 12/2011 | Michelson |
| 8,177,812 | B2 | 5/2012 | Sankaran |
| 8,192,495 | B2 | 6/2012 | Simpson et al. |
| 8,221,501 | B2 | 7/2012 | Eisermann et al. |
| 8,221,502 | B2 | 7/2012 | Branch |
| 8,231,681 | B2 | 7/2012 | Castleman et al. |
| 8,236,058 | B2 | 8/2012 | Fabian et al. |
| 8,241,358 | B2 | 8/2012 | Butler et al. |
| 8,257,442 | B2 | 9/2012 | Edie et al. |
| 8,267,939 | B2 | 9/2012 | Cipoletti et al. |
| 8,273,128 | B2 | 9/2012 | Oh et al. |
| 8,287,599 | B2 | 10/2012 | McGuckin |
| 8,303,663 | B2 | 11/2012 | Jimenez et al. |
| 8,323,345 | B2 | 12/2012 | Sledge |
| 8,328,852 | B2 | 12/2012 | Zehavi et al. |
| 8,337,559 | B2 | 12/2012 | Hansell et al. |
| 8,353,961 | B2 | 1/2013 | McClintock |
| 8,382,842 | B2 | 2/2013 | Greenhalgh et al. |
| 8,398,713 | B2 | 3/2013 | Weiman |
| 8,403,990 | B2 | 3/2013 | Dryer et al. |
| 8,409,291 | B2 | 4/2013 | Blackwell et al. |

(56) References Cited

U.S. PATENT DOCUMENTS

| | | |
|---|---|---|
| 8,435,298 B2 | 5/2013 | Weiman |
| 8,454,617 B2 | 6/2013 | Schaller |
| 8,486,148 B2 | 7/2013 | Butler et al. |
| 8,491,659 B2 | 7/2013 | Weiman |
| 8,506,635 B2 | 8/2013 | Palmatier et al. |
| 8,518,087 B2 | 8/2013 | Lopez et al. |
| 8,518,120 B2 | 8/2013 | Glerum et al. |
| 8,551,173 B2 | 10/2013 | Lechmann et al. |
| 8,556,979 B2 | 10/2013 | Glerum et al. |
| 8,568,481 B2 | 10/2013 | Olmos et al. |
| 8,579,977 B2 | 11/2013 | Fabian |
| 8,579,981 B2 | 11/2013 | Lim |
| 8,591,585 B2 | 11/2013 | McLaughlin et al. |
| 8,628,576 B2 | 1/2014 | Triplett et al. |
| 8,628,578 B2 | 1/2014 | Miller et al. |
| 8,632,595 B2 | 1/2014 | Weiman |
| 8,663,329 B2 | 3/2014 | Ernst |
| 8,668,740 B2 | 3/2014 | Rhoda et al. |
| 8,679,183 B2 | 3/2014 | Glerum et al. |
| 8,685,098 B2 | 4/2014 | Glerum et al. |
| 8,696,751 B2 | 4/2014 | Ashley et al. |
| 8,709,086 B2 | 4/2014 | Glerum et al. |
| 8,715,351 B1 | 5/2014 | Pinto |
| 8,721,723 B2 | 5/2014 | Hansell et al. |
| 8,753,398 B2 | 6/2014 | Gordon et al. |
| 8,771,360 B2 | 7/2014 | Jimenez et al. |
| 8,778,025 B2 | 7/2014 | Ragab et al. |
| 8,795,366 B2 | 8/2014 | Varela |
| 8,828,085 B1 | 9/2014 | Jensen |
| 8,845,731 B2 | 9/2014 | Weiman |
| 8,845,732 B2 | 9/2014 | Weiman |
| 8,845,734 B2 | 9/2014 | Weiman |
| 8,852,279 B2 | 10/2014 | Weiman |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,900,307 B2 | 12/2014 | Hawkins et al. |
| 8,936,641 B2 | 1/2015 | Cain |
| 8,940,052 B2 | 1/2015 | Lechmann et al. |
| 9,095,446 B2 | 8/2015 | Landry et al. |
| 9,095,447 B2 | 8/2015 | Barreiro et al. |
| 2002/0068976 A1 | 6/2002 | Jackson |
| 2002/0068977 A1 | 6/2002 | Jackson |
| 2002/0128716 A1 | 9/2002 | Cohen et al. |
| 2002/0151976 A1 | 10/2002 | Foley et al. |
| 2002/0165612 A1 | 11/2002 | Gerber et al. |
| 2003/0004575 A1* | 1/2003 | Erickson .................. 623/17.15 |
| 2003/0004576 A1 | 1/2003 | Thalgott |
| 2003/0023305 A1 | 1/2003 | McKay |
| 2003/0040799 A1 | 2/2003 | Boyd et al. |
| 2003/0065396 A1 | 4/2003 | Michelson |
| 2003/0078667 A1 | 4/2003 | Manasas et al. |
| 2003/0130739 A1 | 7/2003 | Gerbec et al. |
| 2003/0135275 A1 | 7/2003 | Garcia |
| 2003/0139812 A1* | 7/2003 | Garcia et al. ............. 623/17.11 |
| 2003/0139813 A1 | 7/2003 | Messerli et al. |
| 2003/0233145 A1 | 12/2003 | Landry et al. |
| 2004/0030387 A1 | 2/2004 | Landry et al. |
| 2004/0064144 A1 | 4/2004 | Johnson et al. |
| 2004/0087947 A1 | 5/2004 | Lim |
| 2004/0088055 A1 | 5/2004 | Hanson et al. |
| 2004/0127991 A1 | 7/2004 | Ferree |
| 2004/0153065 A1 | 8/2004 | Lim |
| 2004/0153156 A1 | 8/2004 | Cohen et al. |
| 2004/0162618 A1 | 8/2004 | Mujwid et al. |
| 2004/0172133 A1 | 9/2004 | Gerber et al. |
| 2004/0186570 A1 | 9/2004 | Rapp |
| 2004/0186577 A1 | 9/2004 | Ferree |
| 2004/0230309 A1 | 11/2004 | DiMauro |
| 2005/0038515 A1 | 2/2005 | Kunzler |
| 2005/0113916 A1 | 5/2005 | Branch |
| 2005/0113917 A1 | 5/2005 | Chae et al. |
| 2005/0125062 A1* | 6/2005 | Biedermann et al. ...... 623/17.11 |
| 2005/0222681 A1 | 10/2005 | Richley et al. |
| 2005/0256576 A1 | 11/2005 | Moskowitz et al. |
| 2005/0261769 A1 | 11/2005 | Moskowitz et al. |
| 2005/0278026 A1 | 12/2005 | Gordon et al. |
| 2006/0058876 A1 | 3/2006 | McKinley |
| 2006/0100706 A1 | 5/2006 | Shadduck et al. |
| 2006/0122701 A1 | 6/2006 | Kiester |
| 2006/0122703 A1 | 6/2006 | Aebi et al. |
| 2006/0129244 A1 | 6/2006 | Ensign |
| 2006/0136062 A1 | 6/2006 | DiNello et al. |
| 2006/0142858 A1* | 6/2006 | Colleran et al. ........... 623/17.11 |
| 2006/0206207 A1 | 9/2006 | Dryer et al. |
| 2006/0235531 A1 | 10/2006 | Buettner |
| 2006/0253201 A1 | 11/2006 | McLuen |
| 2006/0265075 A1 | 11/2006 | Baumgartner et al. |
| 2006/0265077 A1 | 11/2006 | Zwirkoski |
| 2007/0010886 A1 | 1/2007 | Banick et al. |
| 2007/0055377 A1* | 3/2007 | Hanson et al. ............. 623/17.11 |
| 2007/0118222 A1 | 5/2007 | Lang |
| 2007/0149978 A1 | 6/2007 | Shezifi et al. |
| 2007/0173939 A1 | 7/2007 | Kim et al. |
| 2007/0191959 A1 | 8/2007 | Hartmann et al. |
| 2007/0198089 A1 | 8/2007 | Moskowitz et al. |
| 2007/0208423 A1 | 9/2007 | Messerli et al. |
| 2007/0219634 A1 | 9/2007 | Greenhalgh et al. |
| 2007/0233244 A1 | 10/2007 | Lopez et al. |
| 2007/0270968 A1 | 11/2007 | Baynham et al. |
| 2007/0276375 A1 | 11/2007 | Rapp |
| 2007/0299521 A1 | 12/2007 | Glenn |
| 2008/0009877 A1 | 1/2008 | Sankaran et al. |
| 2008/0015701 A1 | 1/2008 | Garcia et al. |
| 2008/0021556 A1 | 1/2008 | Edie |
| 2008/0021558 A1 | 1/2008 | Thramann |
| 2008/0027550 A1 | 1/2008 | Link et al. |
| 2008/0033440 A1 | 2/2008 | Moskowitz et al. |
| 2008/0058944 A1 | 3/2008 | Duplessis et al. |
| 2008/0065219 A1 | 3/2008 | Dye |
| 2008/0082173 A1* | 4/2008 | Delurio et al. ............. 623/17.16 |
| 2008/0140207 A1 | 6/2008 | Olmos |
| 2008/0147193 A1 | 6/2008 | Matthis et al. |
| 2008/0167657 A1 | 7/2008 | Greenhalgh |
| 2008/0177388 A1 | 7/2008 | Patterson et al. |
| 2008/0183204 A1 | 7/2008 | Greenhalgh et al. |
| 2008/0195209 A1 | 8/2008 | Garcia et al. |
| 2008/0243251 A1 | 10/2008 | Stad et al. |
| 2008/0243254 A1 | 10/2008 | Butler |
| 2008/0249622 A1* | 10/2008 | Gray .......................... 623/17.11 |
| 2008/0281425 A1* | 11/2008 | Thalgott et al. ............ 623/17.16 |
| 2009/0030423 A1 | 1/2009 | Puno |
| 2009/0054991 A1 | 2/2009 | Biyani |
| 2009/0076610 A1 | 3/2009 | Afzal |
| 2009/0099568 A1 | 4/2009 | Lowry et al. |
| 2009/0112320 A1 | 4/2009 | Kraus |
| 2009/0112324 A1 | 4/2009 | Refai et al. |
| 2009/0222096 A1 | 9/2009 | Trieu |
| 2009/0222099 A1 | 9/2009 | Liu et al. |
| 2009/0234398 A1 | 9/2009 | Chirico et al. |
| 2009/0240335 A1 | 9/2009 | Arcenio et al. |
| 2009/0248159 A1 | 10/2009 | Aflatoon |
| 2009/0292361 A1 | 11/2009 | Lopez et al. |
| 2010/0016905 A1 | 1/2010 | Greenhalgh et al. |
| 2010/0179594 A1 | 7/2010 | Theofilos et al. |
| 2010/0234956 A1 | 9/2010 | Attia et al. |
| 2010/0262240 A1 | 10/2010 | Chavatte et al. |
| 2010/0286783 A1 | 11/2010 | Lechmann et al. |
| 2010/0324607 A1 | 12/2010 | Davis |
| 2011/0004308 A1 | 1/2011 | Marino et al. |
| 2011/0004310 A1 | 1/2011 | Michelson |
| 2011/0015747 A1 | 1/2011 | McManus et al. |
| 2011/0029082 A1 | 2/2011 | Hall |
| 2011/0035011 A1 | 2/2011 | Cain |
| 2011/0093074 A1 | 4/2011 | Glerum et al. |
| 2011/0130835 A1 | 6/2011 | Ashley et al. |
| 2011/0130838 A1 | 6/2011 | Morgenstern et al. |
| 2011/0144753 A1 | 6/2011 | Marchek et al. |
| 2011/0172716 A1 | 7/2011 | Glerum |
| 2011/0270261 A1 | 11/2011 | Mast et al. |
| 2011/0282453 A1 | 11/2011 | Greenhalgh et al. |
| 2011/0301711 A1 | 12/2011 | Palmatier et al. |
| 2011/0301712 A1 | 12/2011 | Palmatier et al. |
| 2012/0004726 A1 | 1/2012 | Greenhalgh et al. |

(56) References Cited

U.S. PATENT DOCUMENTS

| | | | |
|---|---|---|---|
| 2012/0004732 A1 | 1/2012 | Goel et al. |
| 2012/0022654 A1 | 1/2012 | Farris et al. |
| 2012/0029636 A1 | 2/2012 | Ragab et al. |
| 2012/0071977 A1 | 3/2012 | Oglaza et al. |
| 2012/0071980 A1 | 3/2012 | Purcell et al. |
| 2012/0083889 A1 | 4/2012 | Purcell et al. |
| 2012/0123546 A1 | 5/2012 | Medina |
| 2012/0197403 A1 | 8/2012 | Merves |
| 2012/0226357 A1 | 9/2012 | Varela |
| 2012/0290097 A1 | 11/2012 | Cipoletti et al. |
| 2012/0310350 A1 | 12/2012 | Farris et al. |
| 2012/0310352 A1 | 12/2012 | DiMauro et al. |
| 2013/0030536 A1 | 1/2013 | Rhoda et al. |
| 2013/0085572 A1 | 4/2013 | Glerum et al. |
| 2013/0085574 A1 | 4/2013 | Sledge |
| 2013/0116791 A1 | 5/2013 | Theofilos |
| 2013/0123924 A1 | 5/2013 | Butler et al. |
| 2013/0123927 A1 | 5/2013 | Malandain |
| 2013/0138214 A1 | 5/2013 | Greenhalgh et al. |
| 2013/0144387 A1 | 6/2013 | Walker et al. |
| 2013/0144388 A1 | 6/2013 | Emery et al. |
| 2013/0158663 A1 | 6/2013 | Miller et al. |
| 2013/0158664 A1 | 6/2013 | Palmatier et al. |
| 2013/0158667 A1 | 6/2013 | Tabor et al. |
| 2013/0158668 A1 | 6/2013 | Nichols et al. |
| 2013/0158669 A1 | 6/2013 | Sungarian et al. |
| 2013/0173004 A1 | 7/2013 | Greenhalgh et al. |
| 2013/0190876 A1 | 7/2013 | Drochner et al. |
| 2013/0190877 A1 | 7/2013 | Medina |
| 2013/0204371 A1 | 8/2013 | McLuen et al. |
| 2013/0211525 A1 | 8/2013 | McLuen et al. |
| 2013/0211526 A1 | 8/2013 | Alheidt et al. |
| 2013/0310939 A1 | 11/2013 | Fabian et al. |
| 2014/0039622 A1 | 2/2014 | Glerum et al. |
| 2014/0046333 A1 | 2/2014 | Johnson et al. |
| 2014/0058513 A1 | 2/2014 | Gahman et al. |
| 2014/0067073 A1 | 3/2014 | Hauck |
| 2014/0114423 A1 | 4/2014 | Suedkamp et al. |
| 2014/0128977 A1 | 5/2014 | Glerum et al. |
| 2014/0135934 A1 | 5/2014 | Hansell et al. |
| 2014/0142706 A1 | 5/2014 | Hansell et al. |
| 2014/0163683 A1 | 6/2014 | Seifert et al. |
| 2014/0172106 A1 | 6/2014 | To et al. |
| 2014/0180421 A1 | 6/2014 | Glerum et al. |
| 2014/0249629 A1 | 9/2014 | Moskowitz et al. |
| 2014/0249630 A1 | 9/2014 | Weiman |
| 2014/0257484 A1 | 9/2014 | Flower et al. |
| 2014/0257486 A1 | 9/2014 | Alheidt |
| 2014/0303731 A1 | 10/2014 | Glerum et al. |
| 2014/0303732 A1 | 10/2014 | Rhoda et al. |
| 2014/0324171 A1 | 10/2014 | Glerum et al. |

FOREIGN PATENT DOCUMENTS

| | | |
|---|---|---|
| DE | 202008001079 | 3/2008 |
| EP | 1290985 | 3/2003 |
| EP | 1532949 | 5/2005 |
| EP | 1541096 | 6/2005 |
| EP | 1683593 | 7/2006 |
| EP | 1698305 B1 | 8/2007 |
| EP | 1843723 B1 | 3/2010 |
| EP | 2368529 | 9/2011 |
| EP | 2237748 B1 | 9/2012 |
| EP | 2764851 | 8/2014 |
| FR | 2874814 | 3/2006 |
| JP | 2003-526457 | 9/2003 |
| JP | 2006-516456 | 7/2006 |
| JP | 2011-509766 A | 3/2011 |
| WO | WO 95/31158 | 11/1995 |
| WO | WO 97/00054 | 1/1997 |
| WO | WO 00/12033 | 3/2000 |
| WO | WO 00/74605 | 12/2000 |
| WO | WO 01/01895 | 1/2001 |
| WO | WO 2005/112834 | 12/2005 |
| WO | WO 2006/047587 | 5/2006 |
| WO | WO 2006/058281 | 6/2006 |
| WO | WO 2006/065419 | 6/2006 |
| WO | WO 2006/081843 | 8/2006 |
| WO | WO 2007/009107 | 1/2007 |
| WO | WO 2007/028098 | 3/2007 |
| WO | WO 2007/048012 | 4/2007 |
| WO | WO 2008/044057 | 4/2008 |
| WO | WO 2009/092102 | 7/2009 |
| WO | WO 2009/064787 | 8/2009 |
| WO | WO 2009/124269 | 10/2009 |
| WO | WO 2009/143496 | 11/2009 |
| WO | WO 2010/068725 | 6/2010 |
| WO | WO 2010/148112 | 12/2010 |
| WO | WO 2011/142761 | 11/2011 |
| WO | WO 2012/009152 | 1/2012 |
| WO | WO 2012/089317 | 7/2012 |
| WO | WO 2012/135764 | 10/2012 |
| WO | WO 2013/006669 | 1/2013 |
| WO | WO 2013/023096 | 2/2013 |
| WO | WO 2013/025876 | 2/2013 |
| WO | WO 2013/043850 | 3/2013 |
| WO | WO 2013/082184 | 6/2013 |
| WO | WO 2013/158294 | 10/2013 |
| WO | WO 2013/173767 | 11/2013 |
| WO | WO 2013/184946 | 12/2013 |
| WO | WO 2014/018098 | 1/2014 |
| WO | WO 2014/026007 | 2/2014 |
| WO | WO 2014/035962 | 3/2014 |
| WO | WO 2014/088521 | 6/2014 |
| WO | WO 2014/116891 | 7/2014 |

OTHER PUBLICATIONS

Krbec, [Replacement of the vertebral body with an expansion implant (Synex)], Acta Chir Orthop Traumatol Cech, 2002, pp. 158-162, vol. 69(3).
U.S. Appl. No. 61/675,975, filed Jul. 26, 2012, Lechmann et al.
International Patent Application No. PCT/US2013/029014, International Search Report dated Jul. 1, 2013, 7 pages.
Chiang, Biomechanical Comparison of Instrumented Posterior Lumbar Interbody Fusion with One or Two Cages by Finite Element Analysis, Spine, Sep. 2006, pp. E682-E689, vol. 31(19), Lippincott Williams & Wilkins, Inc.
Folman, Posterior Lumbar Interbody Fusion for Degenerative Disc Disease Using a Minimally Invasive B-Twin Expandable Spinal Spacer, Journal of Spinal Disorders & Techniques, Oct. 2003, pp. 455-460, vol. 16(5).
Hunt, Expanable cage placement via a posterolateral approach in lumbar spine reconstructions, Journal of Neurosurgery: Spine, Sep. 2006, pp. 271-274, vol. 5.
Polikeit, The importance of the endplate for interbody cages in the lumbar spine, Eur Spine J, Dec. 2003, pp. 556-561, vol. 12.
Shin, Posterior Lumbar Interbody Fusion via a Unilateral Approach, Yonsei Medical Journal, Jun. 2006, pp. 319-325, vol. 47(3).

* cited by examiner

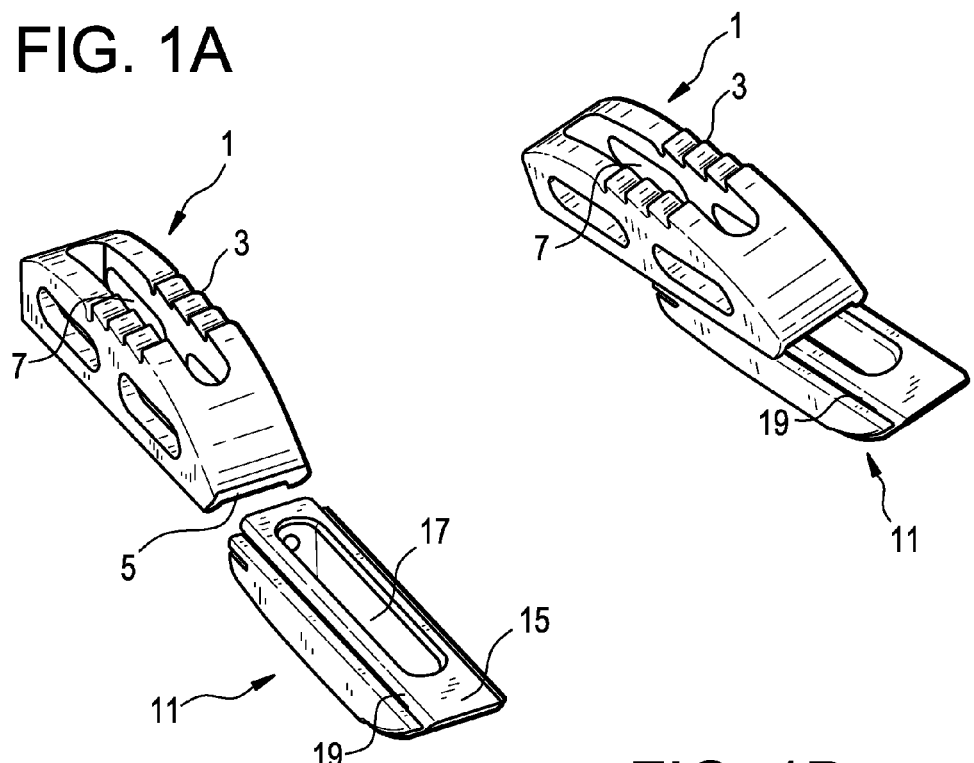
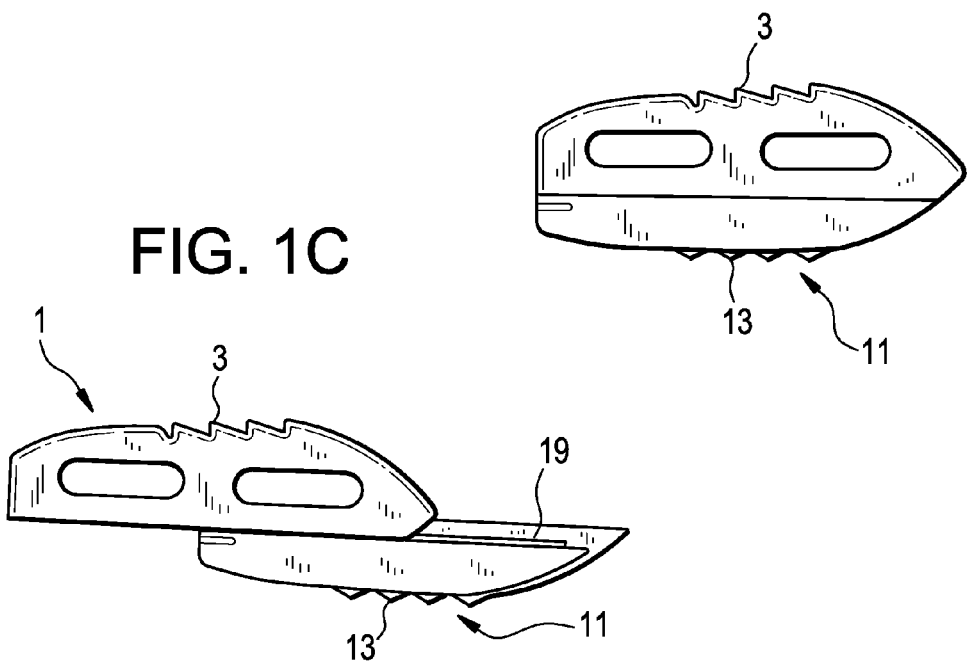

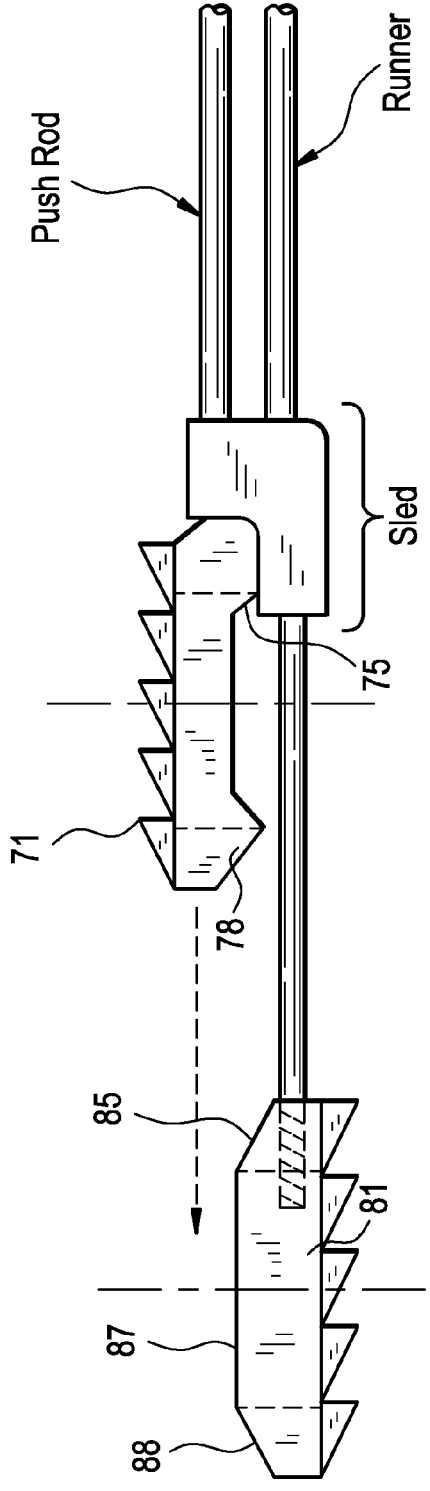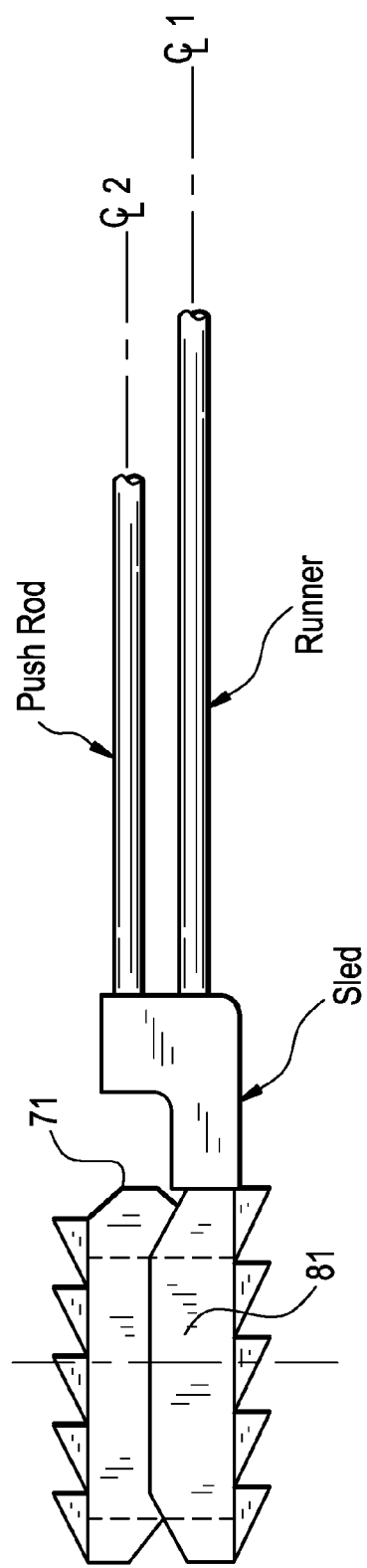

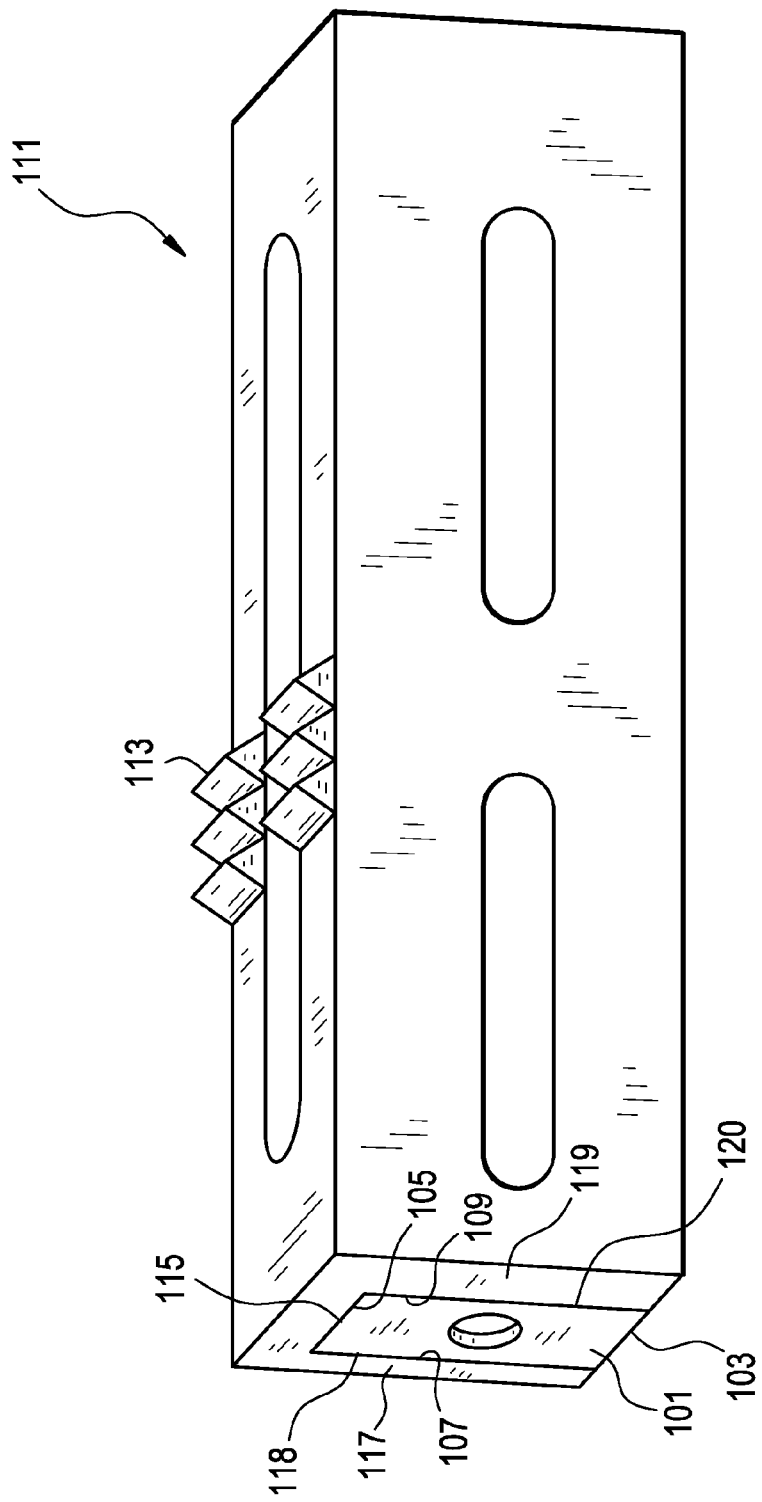

201

203

205

HIGHLY LORDOSED FUSION CAGE

CONTINUING DATA

This divisional application claims priority from co-pending U.S. Ser. No. 11/768,636, entitled "Highly Lordosed Fusion Cage", filed Jun. 26, 2007, by Hawkins et al., the specification of which is incorporated by reference in its entirety.

BACKGROUND OF THE INVENTION

The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus within its cushioning qualities. These nucleus pulposus cells may also secrete small amounts of cytokines such as interleukin-1β and TNF-α as well as matrix metalloproteinases ("MMPs"). These cytokines and MMPs help regulate the metabolism of the nucleus pulposus cells.

In some instances of disc degeneration disease (DDD), gradual degeneration of the intervetebral disc is caused by mechanical instabilities in other portions of the spine. In these instances, increased loads and pressures on the nucleus pulposus cause the cells within the disc (or invading macrophases) to emit larger than normal amounts of the above-mentioned cytokines. In other instances of DDD, genetic factors or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of toxins that may cause nerve irritation and pain.

As DDD progresses, toxic levels of the cytokines and MMPs present in the nucleus pulposus begin to degrade the extracellular matrix, in particular, the MMPs (as mediated by the cytokines) begin cleaving the water-retaining portions of the proteoglycans, thereby reducing its water-retaining capabilities. This degradation leads to a less flexible nucleus pulposus, and so changes the loading pattern within the disc, thereby possibly causing delamination of the annulus fibrosus. These changes cause more mechanical instability, thereby causing the cells to emit even more cytokines, thereby upregulating MMPs. As this destructive cascade continues and DDD further progresses, the disc begins to bulge ("a herniated disc"), and then ultimately ruptures, causing the nucleus pulposus to contact the spinal cord and produce pain.

One proposed method of managing these problems is to remove the problematic disc and replace it with a porous device that restores disc height and allows for bone growth therethrough for the fusion of the adjacent vertebrae. These devices are commonly called "fusion devices".

U.S. Pat. No. 5,865,848 ("Baker") discloses a two piece intervertebral fusion cage having a ramp. Baker describes a intervertebral spacer comprised of two components. The two portions have opposed flanges connected by a screw to effect translation, and complimentary slopes. The components are inserted together in a collapsed condition. Post-insertion translation of one component relative to the other creates an expanded condition and the desired distraction.

US Published Patent Application 2004/0230309 ("DePuy Spine") discloses a two piece intervertebral fusion cage having a ramp. See FIG. 14D.

US Published Patent Application Nos. US2003/0135275 and 2003/0139812 (collectively, "Garcia") disclose a two-piece implant formed by upper and lower halves, wherein the inner surfaces of the two halves form a dovetail joint that runs along a transverse axis of the implant.

SUMMARY OF THE INVENTION

The present invention is directed to a two-piece intervertebral fusion cage, comprising:
 a) an upper component having a first outside surface adapted for gripping an upper vertebral endplate and a first interior surface,
 b) a lower component having a second outside surface adapted for gripping a lower vertebral endplate and a second interior surface,
wherein the interior surfaces mate.

One advantage of such a cage is its easy insertion. In a first step, the lower component is inserted into the disc space and is held in place. The first step confirms placement of the implant and its footprint. In a second step, the upper component is inserted into the disc space by sliding its interior surface along the opposed interior surface of the lower component. This two-step method of insertion eliminates the need to provide an independent distraction means, such as the use of an impaction hammer, and an independent trialing means. It also provides mechanical leverage in the cage to facilitate the creation of lordosis.

A second advantage of such a cage is its impact on patient safety. The gradual nature of the distraction of the disc space provided by this two-step insertion procedure should also reduce the possibility of over-distraction, which can cause neural damage. It also eliminates hammer-induced sudden impaction during cage insertion, thereby reducing cage failures, over-insertion and anterior damage. Lastly, the smaller height of the annular defect produced during device insertion aids in preventing device expulsion.

In a first aspect of the present invention, the outside surface of at least one of the components is substantially parallel to its corresponding interior surface. This provides the advantage of ease of insertion through a small annular defect/incision. Simply, one component can determine height and the other component can determine lordosis.

In a second aspect of the present invention, each component has a throughhole extending from its outside surface to its interior surface, and the interior surfaces of these components mate to align the first and second throughholes. This alignment provides a path for bone growth through the vertical dimension of the device, thereby facilitating fusion between the vertebral endplates.

In a third aspect of the present invention, each component has opposed sidewalls and at least one of the components has a lateral throughhole extending from a sidewall thereof to its opposed sidewall. This lateral throughhole provides a path for increased vascularization, increased diffusion, and bone growth through the lateral dimension of the device, thereby facilitating fusion between the vertebral endplates.

In a fourth aspect of the present invention, each component has a dovetail feature extending along the longitudinal axis of its interior surface and the dovetail features of the corresponding components mate along the longitudinal axes. This mating of dovetails provides for a locking of the mated upper and lower components and increases the assurance that the mated components will not disengage in vivo.

In a fifth aspect of the present invention, the upper component has a tapered distal end, preferably a bulleted nose. This tapered distal end allows for easy distraction of the opposed vertebral endplates upon insertion of the upper component into the disc space.

DESCRIPTION OF THE FIGURES

FIGS. 1a-1d disclose a cage of the present invention having mating dovetail features and aligned vertical throughholes.

FIGS. 5b and 5c disclose a method of inserting the device of FIG. 5a.

FIG. 6 discloses a cage of the present invention wherein one of the components has extending side walls that create a housing adapted to capture the other component.

DETAILED DESCRIPTION OF THE FIGURES

For the purposes of the present invention, the terms "inner surface", "inside surface" "interior surface are interchangeable, as are the terms "exterior surface", "outer surface" and "outside surface".

Figure 1E:
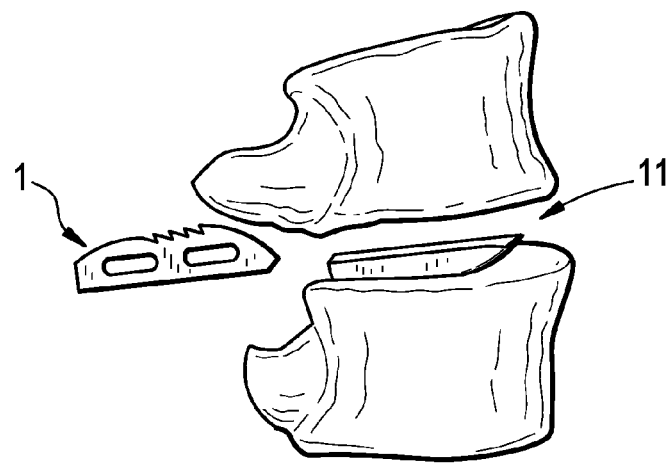
FIGS. 1e-1g disclose the sequential insertion and assembly of the components of the device into the disc space.
Figure 1F:
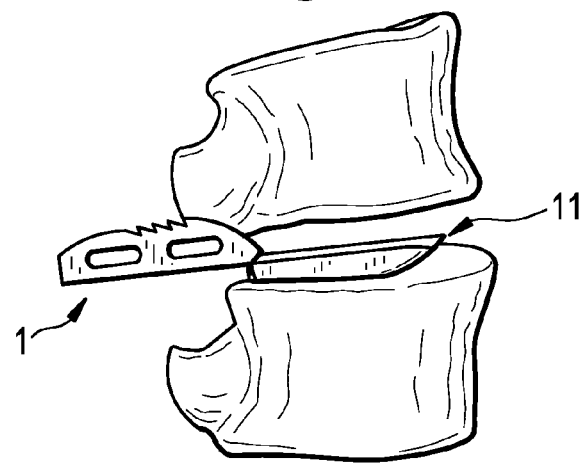
Figure 1G:
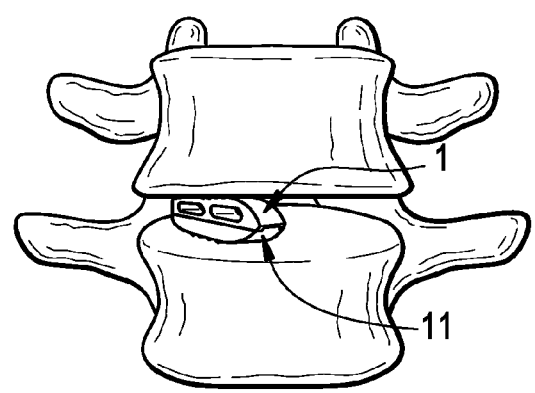

In general, the cage possesses a two-piece structure with hard-endplates and a locking means that is compatible with MIS techniques. Both the top and bottom portions have an interior and exterior surface (FIG. 1), where the exterior surface interfaces with the vertebra.

Now referring to FIGS. 1a-1d, there is provided an intervertebral fusion cage, comprising:
 a) an upper component 1 having a first outside surface 3 adapted for gripping an upper vertebral endplate, a first interior surface 5 having a first longitudinal axis, a first throughhole 7 extending from the outside surface to the first interior surface, and a first dovetail feature (not shown) extending along the first longitudinal axis, and
 b) a lower component 11 having a second outside surface 13 adapted for gripping a lower vertebral endplate, a second interior surface 15 having a second longitudinal axis, a second throughhole 17 extending from the outside surface to the second interior surface, and a second dovetail feature 19 extending along the first longitudinal axis,
wherein the interior surfaces mate to align the first and second throughholes.

The device of FIG. 1 possesses mating dovetail features on its interior surfaces. These features help maintain the device in its assembled form. The device of FIG. 1 also possesses aligned vertical throughholes through each component in its assembled form. These aligned holes help provide desirable bone growth through the device.

In use, the component halves of the device of the present invention are inserted into the disc space is a sequential fashion and are assembled in situ. Now referring to FIG. 1e, the lower component 11 is first inserted into the disc space, with the tapered portion pointing posteriorly, so that it rests upon the floor of the disc space. The reduced height of the lower component allows it to be inserted without any need for distraction. Now referring to FIG. 1f, the inside surface of the upper component is mated to the inside surface of the lower component and advanced into the disc space. Because the height of the combined components is greater than the disc space, and because the nose of the upper component is tapered, gradual insertion of the upper component into the disc space in this manner provides a gradual distraction of the disc space. Now referring to FIG. 1g, the assembled component is located within the disc space.

In one embodiment, the interior surface of the top and/or bottom portion is generally parallel to their exterior surface. Now referring to FIG. 2, there is provided an intervertebral fusion cage, comprising:
 a) an upper component 21 having a first outside surface 23 adapted for gripping an upper vertebral endplate and a first interior surface 25, a first sidewall 27 and a second opposed sidewall (not shown),
 b) a lower component 31 having a second outside surface 33 adapted for gripping a lower vertebral endplate and a second interior surface 35, a third sidewall 37 and a second fourth sidewall (not shown),
wherein the interior surfaces mate,
wherein at least one of the components has a lateral throughhole 39 extending from a sidewall thereof to its opposed sidewall, and
wherein at least one of the outside surfaces is substantially parallel to its corresponding interior surface.

An alternative embodiment would have sloped sides and/or non-parallel throughhole walls. These walls may be curved inwards (concave) or bowed outward (convex). Such an embodiment would increase the mechanical structural stability of the assembled device. Additionally, increasing the devices' mating surface areas would give additional room for the dovetail and locking features. Simultaneously, increased mating surface areas would decrease normal and shear load distributions at the mating surfaces, thereby decreasing likelihood of mechanical failures and further minimizing potential for the generation of particulate wear debris.

Figure 2:
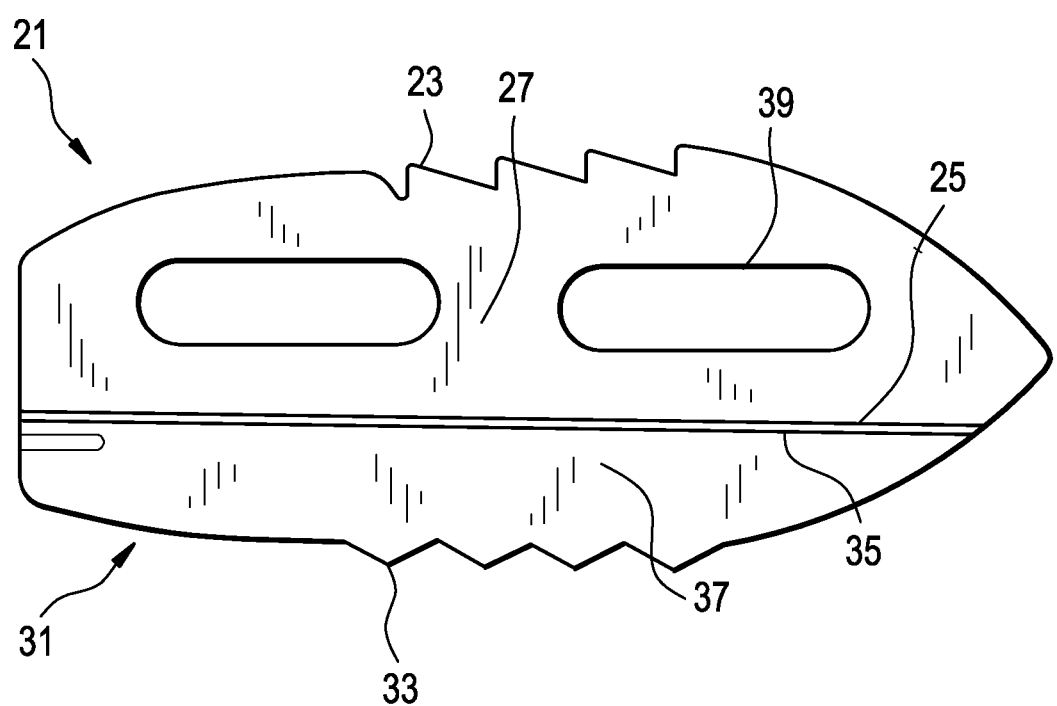
FIG. 2 discloses a cage of the present invention having a lateral throughhole extending from a sidewall thereof to its opposed sidewall, and an outside surfaces that is substantially parallel to its corresponding interior surface.

The device of FIG. 2 possesses a component that has parallel outside and interior surface. The device of FIG. 2 also possesses aligned lateral throughholes through at least one of its components. These holes help in desirable bone growth through the device.

Figure 3:
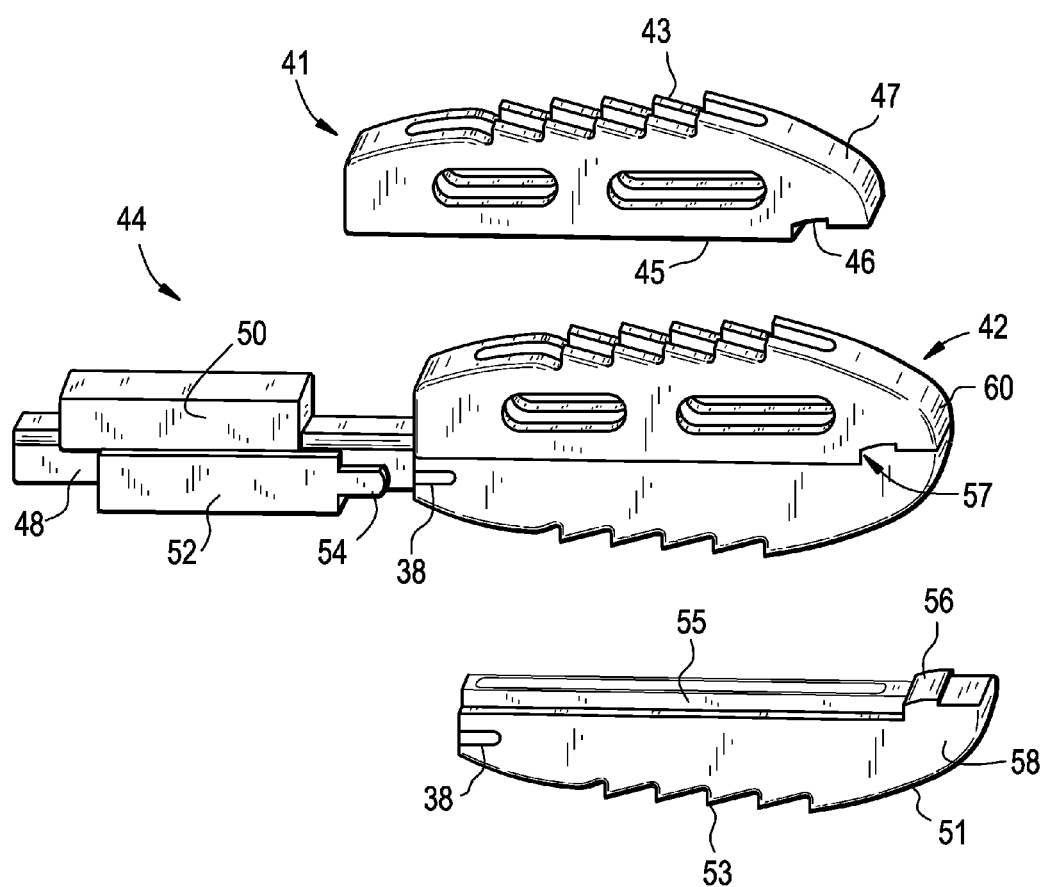
FIG. 3 discloses an exploded cage of the present invention having a bulleted distal nose, along with an assembled cage attached to an insertion instrument.

Now referring to FIG. 3, there is provided the upper 41 and lower 51 halves of the intervertebral fusion cage of the present invention, along with an assembled cage 42 attached to an insertion instrument 44. The intervertebral fusion cage comprises:

a) an upper component 41 having a first outside surface 43 adapted for gripping an upper vertebral endplate, a first interior surface 45 having a recess 46, and a tapered distal end 47, b) a lower component 51 having a second outside surface 53 adapted for gripping a lower vertebral endplate and a second interior surface 55 having a projection 56 and a taper distal end 58, wherein the interior surfaces mate so that the recess and projection form a stop 57 and the tapered distal ends form a bullet nose 60.

The upper component of the device of FIG. 3 possesses a bullet distal nose. This bullet nose helps the upper component distract the disc space as it is inserted into the disc space. The insertion instrument 44 includes a rail 48, a top pusher 50, and a bottom rod 52 having a projection 54 that mates with a recess 38 in the lower component of the cage.

Figure 4:
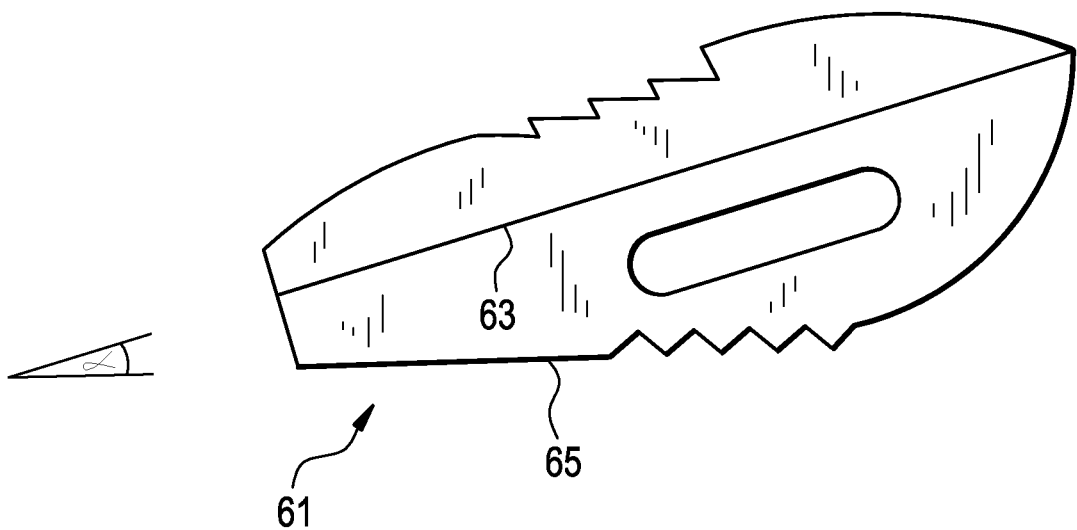
FIG. 4 discloses an interior surface of the lower component that is angled with respect to its corresponding outer surface, thus creating lordosis.

In another embodiment, the interior surface 63 of the lower component 61 creates a ramp having an angle α with respect to its corresponding outer surface 65 (FIG. 4). The upper component 67 of the implant translates along this ramp, creating lordosis.

Because the two pieces of the cage are inserted sequentially into the disc space, the "insertion" height of the assembly and thus the height of the annular defect required during the insertion is approximately one half of the assembled device height.

Figure 5A:
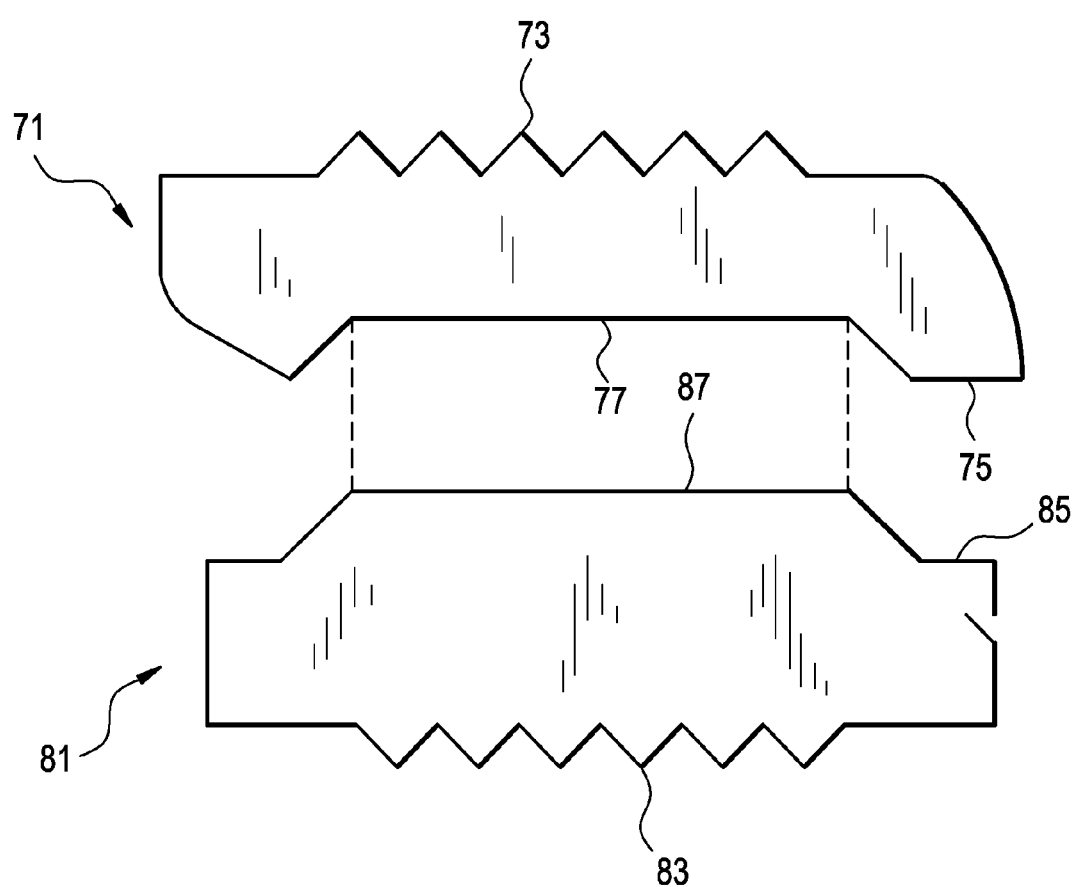
FIG. 5a discloses a cage of the present invention wherein an inside surface of the first component has a recess, and an inside surface of the second component has an extension, wherein the recess and extension mate to provide nesting of the components.

Now referring to FIG. 5a, there is provided an intervertebral fusion cage, comprising:

a) a first component 71 having a first outside surface 73 adapted for gripping a first vertebral endplate, a first interior surface 75, and a recess 77 in the first interior surface extending toward the first outside surface, b) a second component 81 having a second outside surface 83 adapted for gripping a second vertebral endplate, a second interior surface 85, and an extension 87 extending from the second interior surface toward the first interior surface, wherein the recess and extension of the interior surfaces mate to provide nesting of the components.

Now referring to FIGS. 5b and 5c, there is provided a method of inserting the nested cage of FIG. 5a: Place the baseplate 81 in the interbody disc space. Position and slide the overrider plate 71 onto and over the baseplate 81. Initially, the overrider nose 78 will slide across the base plate's interior surface 87 thereby creating a slight over-distraction of the disc space. As the overrider's posterior aspect 75 approaches the baseplate's posterior niche 85, the anterior overrider nose 78 will fall into the anterior niche 88 thereby providing a positive stop and locking mechanism to seat the overrider plate 71 onto the baseplate 81.

The preferred method for the order of insertion of the two-piece cage of the present invention is now disclosed. The first step can be placement of the first component of the device against the inferior vertebral body. This is often followed by insertion and eventual assembly of the second component onto and over the first component. The first component should contain a lordosed or angled component such that the surface over which the second component is inserted is substantially parallel to the superior vertebral endplate.

Alternatively, the method of inserting the first component with substantially parallel bone contacting and interior surfaces requires that the second component to contain a lordotic angle. As this two-piece assembled cage is typically inserted from a posterior approach, and the angle of the interbody cavity widens anteriorly, insertion of the second component with a lordotic angle requires over-distraction of the posterior aspect of the interbody space to accommodate the larger/taller anterior aspect of the second component. This over-distraction and the associated increased insertion force is not associated with the preferred method where the lordosed component is inserted first followed by the height-restoring component with substantially parallel sides.

Now referring to FIG. 6, there is provided an intervertebral fusion cage, comprising:

a) a first component 101 having a first outside surface 103 adapted for gripping an upper vertebral endplate and a first interior surface 105, a first sidewall 107 extending between the first outside surface and the first interior surface and having an outer surface (not shown) and a second opposed sidewall 109 extending between the first outside surface and the first interior surface and having an outer surface (not shown), b) a housing component 111 having a second outside surface 113 adapted for gripping a lower vertebral endplate and a second interior surface 115, a third sidewall 117 extending from the second interior surface and away from the second outside surface and having an inner surface 118, and a fourth sidewall 119 extending from the second interior surface and away from the second outside surface and having an inner surface 120, wherein the interior surfaces mate, and wherein the outer surfaces of the first component mates with their respective inner surfaces of the housing component.

In FIG. 6, one of the components has extending side walls that create a housing adapted to capture the other component. The advantage of this embodiment is that it possesses an enhanced dovetail creating enhanced stability.

Figure 7A:
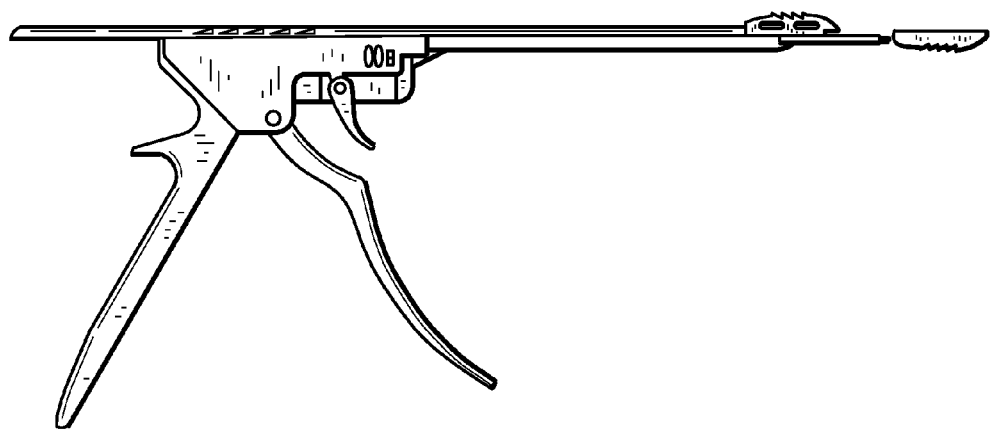
FIGS. 7a and 7b disclose the device of the present invention attached to an insertion instrument.
Figure 7B:
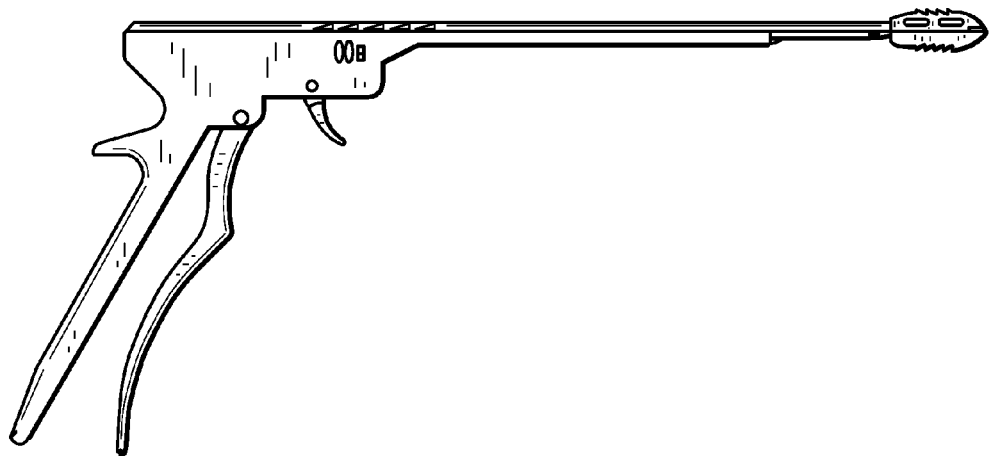

Now referring to FIGS. 7a-b, there is provided a device for inserting the components of the present invention into the disc space. FIG. 7a discloses the disposition of the instrument during insertion of the inferior component into the disc space. FIG. 7b discloses the disposition of the device when the upper component is advanced into the disc space to the point where it rides on top of the lower component and forms the assembly.

The endplates may have teeth to prevent migration and perforations to allow bone growth.

Radiographic markers can be incorporated to allow intra- or post-operative visualization.

Additionally, the outside surfaces of the superior and inferior portions can be designed with varying geometries to allow for their customization to the patient's anatomy, thereby minimizing the risk of subsidence. For instance, the outside surface of the superior half may have a convex dome while the outside surfaces of the inferior half may be flat, convex, concave or serpentine (concave posterior and convex anterior).

Figure 8A:
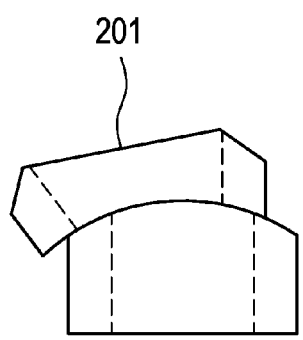
FIGS. 8a-8c disclose arcuate cages of the present invention.
Figure 8B:
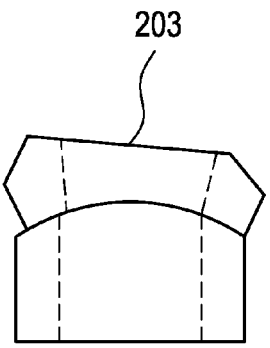
Figure 8C:
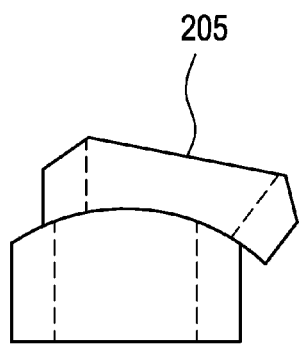
Figure 8D:
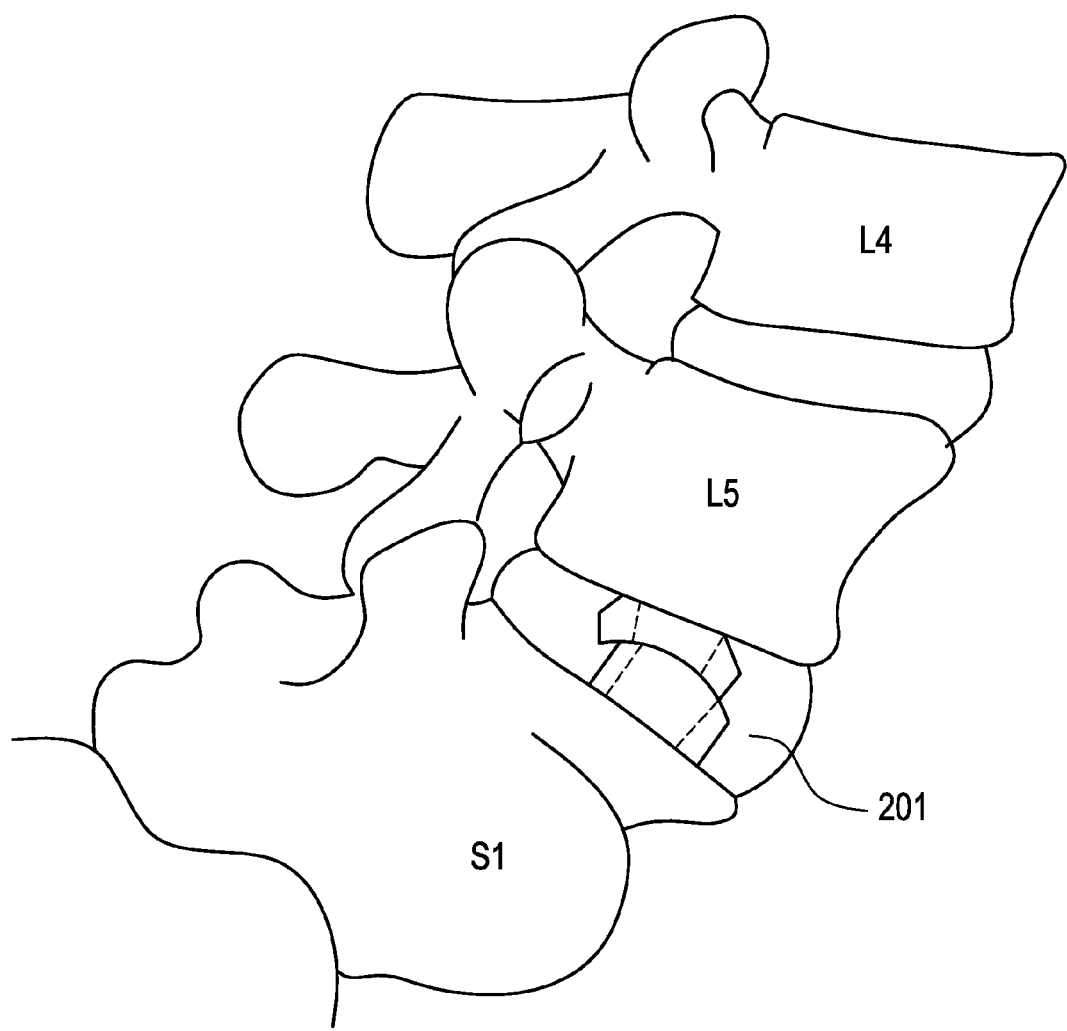
FIG. 8d discloses an arcuate cage inserted into a disc space.

In an alternative embodiment, an arcuate sliding mating pathway is contemplated. FIGS. 8a-8c disclose arcuate cages of the present invention forming a lordotic angle 201 (FIG. 8a), no angle 203 (FIG. 8b) and a kyphotic angle 205 (FIG. 8c). FIG. 8d discloses a lordotic arcuate cage 201 inserted into a disc space.

The benefit to assembling the two cage halves using an arcuate assembly pathway is the potential to provide in situ determination of lordotic angle. Also, the arcuate pathway would embody a mechanism allowing a continuously variable lordotic angle (as opposed to discrete lordotic angles represented by assembly of different superior or inferior cage components). The arcuate mating mechanism requires that one half of the cage contains a convex mating surface while the other half contains a concave mating surface with an arcuate geometry that exactly mimics the inverse of the opposite curve. The assembled halves would represent a fixed radial distance about some center of rotation (the geometric centroid of the arcuate pathway). This fixed radial distance represents the cage height. As the superior cage half slides along the arcuate mating surface of the inferior cage half, the lordotic angle of the assembly will vary continuously. Detents, stops, or teeth can be inserted into the arcuate pathway to create discrete increments of lordotic angles along the continuous arcuate pathway, if this is a preferred further embodiment.

The arcuate pathway enables similar seating features compared to the planar device mating pathway—dovetails, keyways, detents, snap-fits, set screws, etc.

The two halves of the device may be secured together by various means. For instance, a dovetail feature may be incorporated into the interior surfaces of the top and bottom portions for ease of insertion, as shown in FIGS. 1a-f, 2 and 3. The two components may also be stacked and nested together without a dovetail, as shown in FIGS. 5a-c, or the superior/inferior half may have side walls creating a housing that captures the other portion, as shown in FIG. 6. The two portions of the device may be locked together in a variety of locking means including but not limited to Morse taper locks, positive stop(s), ultrasonic welding, snap mechanism(s), a set screw, a clip, a collet, cams, etc. Additional design features can be included to aid in seating the two halves: mechanical keys, a threaded nut can screw onto threaded features on the posterior aspect of each half, and a mechanical channel can be incorporated into the design for the use of curing compounds like adhesives and grouts.

Both components of the device may also incorporate a variety of holding means to assist during the insertion of the device. These holding means may be located on the interior or exterior surfaces as well as along the sidewalls. For example, the top and/or bottom portion may have threaded holes, divots, or slots to provide for secure holding and cage support during insertion, placement and assembly.

After placing the inferior portion, the superior portion can be inserted by several means to expand the overall device height and provide appropriate lordosis or kyphosis.

The superior and inferior portions are generally hollow to provide for filling with various osteogenic fillers and can be porous to allow for graft filling, bony ingrowth and spinal fusion. Lateral openings can also be incorporated to increase vascularization of the osteogenic fillers as well as to provide post-operative visualization of the bony fusion process. Filling can be done preoperatively or intraoperatively, as a through hole into the wedge can facilitate filling of the entire construct in situ Unlike traditional single-piece cages, the two-piece assembled cage requires sliding articulation of two half-cages packed with bone. Bone packed within a cage is typically held in place using friction forces. The sliding assembly mechanisms described could potentially dislodge packed bone graft during cage insertion and/or assembly. To mitigate the dislodgement of bone chips or the potential for sliding-interference of the bone chips, bonding a resorbable lamina of material between the two halfs is proposed. Such a lamina could be placed on the interior surface 45 of the upper half 43 (see FIG. 3). Such a resorbable member could be applied to all cage openings but is of particular utility to prevent dislodgement or interference of the bone graft during sliding assembly of the two halves.

The present invention also offers novel trialing methods. The inferior or superior portion of the implant device can be inserted alone to confirm disc space clearance and device placement, and a trial of the superior component can be placed upon the inserted component to confirm disc height, lordosis, and placement.

Because these cages reduce the profile required for their insertion, they allow for implantation through a cannula that may be smaller than the conventional cannula.

The endplates can be made of any structural biocompatible material including resorbable (PLA, PLGA, etc.), non-resorbable polymers (CFRP, PEEK, UHMWPE, PDS), metallics (SS, Ti-6Al-4V, CoCr, etc.), as well as materials that are designed to encourage bony regeneration (allograft, bone substitute-loaded polymers, growth factor-loaded polymers, ceramics, etc.). The materials for the upper and lower components are biocompatible and generally similar to those disclosed in the prior art. Examples of such materials are metal, PEEK and ceramic.

In preferred embodiments, each of the upper and lower components is manufactured from a material that possesses the desirable strength and stiffness characteristics for use as a fusion cage component.

These components of the present invention may be made from any non-resorbable material appropriate for human surgical implantation, including but not limited to, surgically appropriate metals, and non-metallic materials, such as carbon fiber composites, polymers and ceramics.

In some embodiments, the cage material is selected from the group consisting of PEEK, ceramic and metallic. The cage material is preferably selected from the group consisting of metal and composite (such as PEEK/carbon fiber).

If a metal is chosen as the material of construction for a component, then the metal is preferably selected from the group consisting of titanium, titanium alloys (such as Ti-6Al-4V), chrome alloys (such as CrCo or Cr—Co—Mo) and stainless steel.

If a polymer is chosen as a material of construction for a component, then the polymer is preferably selected from the group consisting of polyesters, (particularly aromatic esters such as polyalkylene terephthalates, polyamides; polyalkenes; poly(vinyl fluoride); PTFE; polyarylethyl ketone PAEK; polyphenylene and mixtures thereof.

If a ceramic is chosen as the material of construction for a component, then the ceramic is preferably selected from the group consisting of alumina, zirconia and mixtures thereof. It is preferred to select an alumina-zirconia ceramic, such as BIOLOX Delta™, available from CeramTec of Plochingen, Germany. Depending on the material chosen, a smooth surface coating may be provided thereon to improve performance and reduce particulate wear debris.

In some embodiments, the cage member comprises PEEK. In others, it is a ceramic.

In some embodiments, the first component consists essentially of a metallic material, preferably a titanium alloy or a chrome-cobalt alloy. In some embodiments, the second component consists essentially of the same metallic material as the first plate.

In some embodiments, the components are made of a stainless steel alloy, preferably BioDur® CCM Plus® Alloy available from Carpenter Specialty Alloys, Carpenter Technology Corporation of Wyomissing, Pa. In some embodiments, the outer surfaces of the components are coated with a sintered beadcoating, preferably Porocoat™, available from DePuy Orthopaedics of Warsaw, Ind.

In some embodiments, the components are made from a composite comprising carbon fiber. Composites comprising carbon fiber are advantageous in that they typically have a strength and stiffness that is superior to neat polymer materials such as a polyarylethyl ketone PAEK. In some embodiments, each component is made from a polymer composite such as a PEKK-carbon fiber composite.

Preferably, the composite comprising carbon fiber further comprises a polymer. Preferably, the polymer is a polyarylethyl ketone (PAEK). More preferably, the PAEK is selected from the group consisting of polyetherether ketone (PEEK), polyether ketone ketone (PEKK) and polyether ketone (PEK). In preferred embodiments, the PAEK is PEEK.

In some embodiments, the carbon fiber comprises between 1 vol % and 60 vol % (more preferably, between 10 vol % and 50 vol %) of the composite. In some embodiments, the polymer and carbon fibers are homogeneously mixed. In others, the material is a laminate. In some embodiments, the carbon fiber is present in a chopped state. Preferably, the chopped carbon fibers have a median length of between 1 mm and 12 mm, more preferably between 4.5 mm and 7.5 mm. In some embodiments, the carbon fiber is present as continuous strands.

In especially preferred embodiments, the composite comprises:
 a) 40-99% (more preferably, 60-80 vol %) polyarylethyl ketone (PAEK), and
 b) 1-60% (more preferably, 20-40 vol %) carbon fiber,
wherein the polyarylethyl ketone (PAEK) is selected from the group consisting of polyetherether ketone (PEEK), polyether ketone ketone (PEKK) and polyether ketone (PEK).

In some embodiments, the composite consists essentially of PAEK and carbon fiber. More preferably, the composite comprises 60-80 wt % PAEK and 20-40 wt % carbon fiber. Still more preferably the composite comprises 65-75 wt % PAEK and 25-35 wt % carbon fiber.

Although the present invention has been described with reference to its preferred embodiments, those skillful in the art will recognize changes that may be made in form and structure which do not depart from the spirit of the invention.

Alternatively, combinations of cage materials could be beneficial (i.e.,—a ceramic bottom half with a PEEK top half).

We claim:
1. An intervertebral fusion cage, comprising:
 a) a first component having an outside surface configured to engage an upper vertebral endplate, an interior surface opposite the outside surface along a first direction, and a tapered first distal end, wherein the first component defines a recess that extends into the interior surface toward the outside surface;
 b) a second component having first and second opposed surfaces that are opposite each other along the first direction, and a second distal end, wherein the second component includes a projection that extends from the first surface along the first direction away from the second surface,
 wherein the first surface is slidable along the interior surface in a second direction perpendicular to the first direction such that the second distal end travels toward the tapered first distal end until the projection is received in the recess so as to impede the first surface from further sliding along the interior surface in the second direction, and
 wherein the projection defines first and second ends that are offset from each other a linear distance along a third direction that is greater than each of a height of the projection along the first direction and a width of the projection along the second direction, and the third direction is perpendicular to each of the first and second directions.

2. The intervertebral fusion cage of claim 1, configured to be inserted into an intervertebral space defined by the upper vertebral endplate and a second vertebral endplate, and the second component urges the first component to move the upper vertebral endplate away from the second vertebral endplate as the first surface slides along the interior surface.

3. The intervertebral fusion cage of claim 1, wherein the second component defines a proximal end opposite the second distal end along a central longitudinal axis that is oriented along the second direction.

4. The intervertebral fusion cage of claim 1, wherein the second component defines first and second opposed side walls that are spaced from each other along the third direction, and extend from the first surface to the second surface, and the projection is elongate from the first side wall to the second side wall.

5. The intervertebral fusion cage of claim 4, wherein the outside surface and the interior surface of the first component are opposite each other along the first direction, and the recess is elongate along the third direction.

6. The intervertebral fusion cage of claim 5, wherein the second direction is a straight direction.

7. The intervertebral fusion cage of claim 5, wherein the recess extends into the interior surface along the first direction and terminates without extending through to the outside surface.

8. The intervertebral fusion cage of claim 1, wherein the first component has a first throughhole extending from the outside surface to the interior surface.

9. The intervertebral fusion cage of claim 8, wherein the second component has a second throughhole extending from the first opposed surface to the second opposed surface.

10. The intervertebral fusion cage of claim 1, wherein the first component has first and second opposed surfaces that extend from the outside surface to the interior surface, and the first component defines a plurality of throughholes extending from the first side surface to the second side surface.

11. The intervertebral fusion cage of claim 1, wherein the outside surface is tapered toward the interior surface at the tapered first distal end.

12. The intervertebral fusion cage of claim 1, wherein the first and second opposed surfaces are opposite each other along the first direction.

13. The intervertebral fusion cage of claim 1, wherein the first component is elongate along the second direction, and the outside surface of the first component defines a plurality of ridges that are oriented generally along the third direction.

14. The intervertebral fusion cage of claim 13, wherein the ridges are spaced from each other along the second direction.

15. The intervertebral fusion cage of claim 14, wherein the ridges are parallel to each other.

16. The intervertebral fusion cage of claim 1, wherein the projection extends linearly from the first end to the second end.

17. The intervertebral fusion cage of claim 16, wherein the projection extends linearly along the third direction from the first end to the second end.

18. The intervertebral fusion cage of claim 1, wherein the first surface faces the interior surface as the first surface slides along the interior surface in the second direction.

19. An intervertebral fusion cage, comprising:
 a) a first component having a first outside surface and a first interior surface that faces opposite the first outside surface, a first outer surface that extends from the first outside surface to the first interior surface, and a second outer surface opposite the first outer surface along a first direction, wherein the second outer surface extends from the first outside surface to the first interior surface, and the first interior surface extends from the first outer surface to the second outer surface; and b) a housing component having a second outside surface configured to engage a vertebral endplate and a second interior surface that faces opposite the second outside surface, a first sidewall extending from the second interior surface and away from the second outside surface, and a second sidewall extending from the second interior surface and away from the second outside surface, wherein the first side wall is opposite the second side wall along the first direction, wherein the first component is configured for insertion into the housing component such that an entirety of the first interior surface is disposed between the first and second sidewalls with respect to the first direction, and the first interior surface abuts the second interior surface.

20. The intervertebral fusion cage of claim 19, wherein the first outside surface and the second outside surface are spaced from each other along a second direction that is perpendicular to the first direction, and the first interior surface abuts the second interior surface when the first component is inserted into the housing component along a third direction that is perpendicular to each of the first and second directions.

21. The intervertebral fusion cage of claim 19, wherein the housing component defines a throughhole that extends from the second outside surface to the second interior surface, and a plurality of throughholes that extend through the second sidewall.

22. The intervertebral fusion cage of claim 19, wherein the first component defines an enclosed aperture is entirely disposed within a perimeter defined by the first outside surface, the first interior surface, the first outer surface, and the second outer surface.

23. The intervertebral fusion cage of claim 19, wherein the first interior surface is parallel to the second interior surface.

24. The intervertebral fusion cage of claim 19, wherein a line oriented along the first direction intersects each of the first and second sidewalls and each of the first and second outer surfaces.

25. The intervertebral fusion cage of claim 19, wherein the first interior surface rides along the second interior surface as the first component is inserted into the housing.

26. The intervertebral fusion cage of claim 19, wherein the first component is configured for insertion into the housing component such that an entirety of the first interior surface is aligned with each of the first and second sidewalls along the first direction.

27. The intervertebral fusion cage of claim 19, wherein each of the first outside surface and the first interior surface is planar.

28. The intervertebral fusion cage of claim 27, wherein each of the second outside surface and the second interior surface is planar.

29. The intervertebral fusion cage of claim 28, wherein the first outside surface and the first interior surface are parallel to each other and to each of the second outside surface and the second interior surface.

30. The intervertebral fusion cage of claim 19, wherein the first outer surface extends continuously from the first outside surface to the first interior surface.

* * * * *